US012133965B2

(12) United States Patent
Chassot et al.

(10) Patent No.: US 12,133,965 B2
(45) Date of Patent: Nov. 5, 2024

(54) INJECTION SYSTEM AND DAY SET ASSEMBLY THEREFOR

(71) Applicant: ACIST MEDICAL SYSTEMS INC., Eden Prairie, MN (US)

(72) Inventors: Pierre-Yves Chassot, Thoiry (FR); Francois Vulliet, Evian (FR)

(73) Assignee: ACIST MEDICAL SYSTEMS INC., Eden Prairie, MN (US)

( * ) Notice: Subject to any disclaimer, the term of this patent is extended or adjusted under 35 U.S.C. 154(b) by 960 days.

(21) Appl. No.: 17/262,451

(22) PCT Filed: Jul. 23, 2019

(86) PCT No.: PCT/EP2019/069794
§ 371 (c)(1),
(2) Date: Jan. 22, 2021

(87) PCT Pub. No.: WO2020/020884
PCT Pub. Date: Jan. 30, 2020

(65) Prior Publication Data
US 2021/0299350 A1    Sep. 30, 2021

(30) Foreign Application Priority Data

Jul. 25, 2018 (EP) .................................. 18185442

(51) Int. Cl.
*A61M 1/14*    (2006.01)
*A61M 5/00*    (2006.01)
(Continued)

(52) U.S. Cl.
CPC ........ *A61M 5/14228* (2013.01); *A61M 5/007* (2013.01); *A61M 5/1408* (2013.01); *A61M 39/10* (2013.01)

(58) Field of Classification Search
CPC .............. A61M 5/1407; A61M 5/1413; A61M 5/1818; A61M 5/14228
See application file for complete search history.

(56) References Cited

U.S. PATENT DOCUMENTS

2009/0105629 A1    4/2009    Grant et al.
2014/0208251 A1    7/2014    Houde et al.
(Continued)

OTHER PUBLICATIONS

International Search Report and Written Opinion for PCT/EP2019/069794, mailed Oct. 22, 2019.

*Primary Examiner* — Courtney B Fredrickson
(74) *Attorney, Agent, or Firm* — VIVICAR Law, PLLC (57) ABSTRACT

A solution for injecting one or more fluids into a patient is proposed. A corresponding injection system comprises: at least one supply station for supplying a fluid to be injected into a patient's vasculature: a pressurizing unit comprising a motor for pressurizing the fluid received from said at least one supply station: a delivery arrangement in fluid communication with said at least one supply station, the delivery arrangement comprising a connector having a connecting element and a latching mechanism: a patient set assembly in fluid communication with said delivery arrangement, said patient set assembly comprising a peristaltic pump component and at least one delivery tube for delivering the pressurized fluid to the patient, said peristaltic pump component having a connecting element for fluidically engaging the connecting element of the connector of the delivery arrangement at said port of the pressurizing unit, characterized in that said latching mechanism comprises an elongated flap integral with said connector, and said latching mechanism engages a corresponding port of the pressurizing unit.

15 Claims, 7 Drawing Sheets

(51) Int. Cl.
*A61M 5/14* (2006.01)
*A61M 5/142* (2006.01)
*A61M 39/10* (2006.01)

(56) References Cited

U.S. PATENT DOCUMENTS

| | | | |
|---|---|---|---|
| 2015/0174320 A1* | 6/2015 | Grant | A61M 5/162 |
| | | | 604/535 |
| 2015/0209515 A1 | 7/2015 | Houde et al. | |
| 2016/0331891 A1 | 11/2016 | Marshall et al. | |

* cited by examiner

PRIOR ART

PRIOR ART

INJECTION SYSTEM AND DAY SET ASSEMBLY THEREFOR

CROSS-REFERENCE TO RELATED APPLICATIONS

This application is the national stage application of corresponding international application number PCT/EP2019/069794, filed Jul. 23, 2019, which claims priority to and the benefit of European application no. 18185442.3, filed Jul. 25, 2018, which is hereby incorporated by reference in its entirety.

TECHNICAL FIELD

The present disclosure relates to the field of medical devices. More specifically, the present disclosure relates to injection systems for delivering a medical fluid to a patient.

BACKGROUND ART

The background of the present disclosure is hereinafter introduced with the discussion of techniques relating to its context. However, even when this discussion refers to documents, acts, artifacts and the like, it does not suggest or represent that the discussed techniques are part of the prior art or are common general knowledge in the field relevant to the present disclosure.

The injection of fluids into patients is commonplace in several medical procedures. For example, a contrast agent (or contrast medium) may be injected, possibly along with a saline solution, to enhance contrast of target (body) features (for example, human body's structures or organs) within the patients in scan examinations thereof. Particularly, in imaging applications (wherein a visual representation of the interior of the patients is created in a non-invasive way without turning to surgery techniques) the use of the contrast agent makes the target features more conspicuous. As a result, target features that would otherwise be less distinguishable from other nearby features (for example, surrounding tissues) are highlighted. This significantly facilitates the task of clinicians in diagnostic applications, and particularly the identification and/or characterization of lesions, the monitoring of their evolution or response to medical treatments. For example, a iodine-based contrast agent (such as comprising iopamidol) is commonly used in Computed Tomography (CT) applications (such as for angiography investigations).

The contrast agent is usually injected into a blood vessel of a patient by an (automated) injection system. The injection system pressurizes the contrast agent (supplied from a corresponding container) and injects it into the patient under predetermined injection conditions, for example, at a predetermined flow rate and volume. In this way, the contrast agent may be injected in a controlled, safe and efficient manner.

Document US 2014/0208251 discloses an automated injection system for injecting fluid into hollow anatomical structure such as blood vessel, artery, vein and heart chamber during medical procedures such as angioplasty. The automated injection system disclosed in this application advantageously provides physicians with a simplified interface for selecting fluid sources, such as saline, contrast, or a mixture of both, to inject at high pressures. The injector system may comprise a multi-use subassembly, a single-use subassembly, a fitting to fluidly connect the multi-use and single-use subassemblies, a hand-held controller, a user interface, and an injector housing.

The automated injection systems known in the art and presently available on the market are divided into two main groups: syringe injectors (like Empower CTA or Empower CTA+ manufactured by Bracco Injeneering SA) and syringe-less injectors (like CT Exprès manufactured by Bracco Injeneering SA).

The present disclosure is directed to syringe-less injectors where the pressurizing unit is provided with a peristaltic pump that houses a plurality of rollers, among which a delivery tube is inserted, and sequentially and alternately squeezed for finally injecting a medical fluid (i.e. a contrast agent or two different contrast agents, a saline solution or a mixture thereof) into a patient.

An injection system is typically provided with one or more supply stations for supplying a contrast agent and/or a saline solution from a corresponding container (e.g. a bottle, a bag or a pouch). The injection system is further provided with a delivery arrangement that is in fluid communication with the at least one supply station and a pressurizing unit. Since the delivery arrangement is positioned upstream of the pressurizing unit and, therefore, it is not in direct connection with a patient, with substantially no risk or a very low risk of cross-contamination, generally the delivery arrangement is a disposable element that is changed periodically (for example, every 10 or 12 hours). This means that the delivery arrangement is not changed when a new patient undergoes an examination, indeed it is typically kept in place for multiple successive injections till the predetermined period of time designed for the delivery arrangement is fully elapsed.

The delivery arrangement (also indicated by the operators as "day set" assembly) is fluidically connected to the pressurizing unit by means of a connector which releasably engages a corresponding port of said pressurizing unit, said connector also being put in fluid communication with a "patient set" assembly for delivering the pressurized fluid into a patient's vasculature. As mentioned above, since the delivery arrangement is a disposable element which is requested to engage the pressurizing unit and successively to disengage from it when a new delivery arrangement has to be installed, the connector is provided with a latching mechanism that is required to guarantee a proper and robust connection with the pressurizing unit dedicated port, and to be easily and efficiently operated by a user while setting up the injection system to be ready for injecting.

The Applicant has perceived the need of improving the current latching mechanism, especially in terms of easiness of operation by the appointed personnel during the connector engagement to and disengagement from the pressurizing unit as well as in terms of improved connection reliability during operation of the injection system, and also in terms of improved and more efficient manufacturing process of the connector itself.

Furthermore, the currently used delivery arrangement comprises inlet ports on opposite lateral sides of the connector body for receiving the tubes (transfer line) of the delivery arrangement, said tubes being fluidically connected to the fluid(s) supply station(s) of the injector system. Typically, at least one of said inlet ports receives a Y-tube connector for guiding two distinct tubes of the delivery arrangement into the same inlet port of the connector body.

The Applicant has thus perceived the need of modifying the design of the current delivery arrangement in order to improve the flow stability and homogeneity of the fluid(s) entering the connector as well as to reduce the overall number of components of the delivery arrangement, thereby simplifying the manufacturing process thereof and reducing the associated costs.

SUMMARY

A simplified summary of the present disclosure is herein presented in order to provide a basic understanding thereof; however, the sole purpose of this summary is to introduce some concepts of the disclosure in a simplified form as a prelude to its following more detailed description, and it is not to be interpreted as an identification of its key elements nor as a delineation of its scope.

The present disclosure relates to an injection system comprising a delivery arrangement which includes a connector provided with an improved latching mechanism that ensures a user friendly and reliable positioning and operation of the connector. In particular, according to an aspect of the present disclosure, the latching mechanism is integral with the connector body and it comprises an elongated flap protruding outwardly from the connector body.

More specifically, one or more aspects of the present disclosure are set out in the independent claims and advantageous features thereof are set out in the dependent claims, with the wording of all the claims that is herein incorporated verbatim by reference (with any advantageous feature provided with reference to any specific aspect that applies mutatis mutandis to every other aspect).

BRIEF DESCRIPTION OF THE DRAWINGS

The solution of the present disclosure, as well as further features and the advantages thereof, will be best understood with reference to the following detailed description thereof, given purely by way of a non-restrictive indication, to be read in conjunction with the accompanying drawings (wherein, for the sake of simplicity, corresponding elements are denoted with equal or similar references and their explanation is not repeated, and the name of each entity is generally used to denote both its type and its attributes, such as value, content and representation). In this respect, it is expressly intended that the figures are not necessary drawn to scale (with some details that may be exaggerated and/or simplified) and that, unless otherwise indicated, they are merely used to illustrate the structures and procedures described herein conceptually. Particularly.

DETAILED DESCRIPTION

Figure 1:
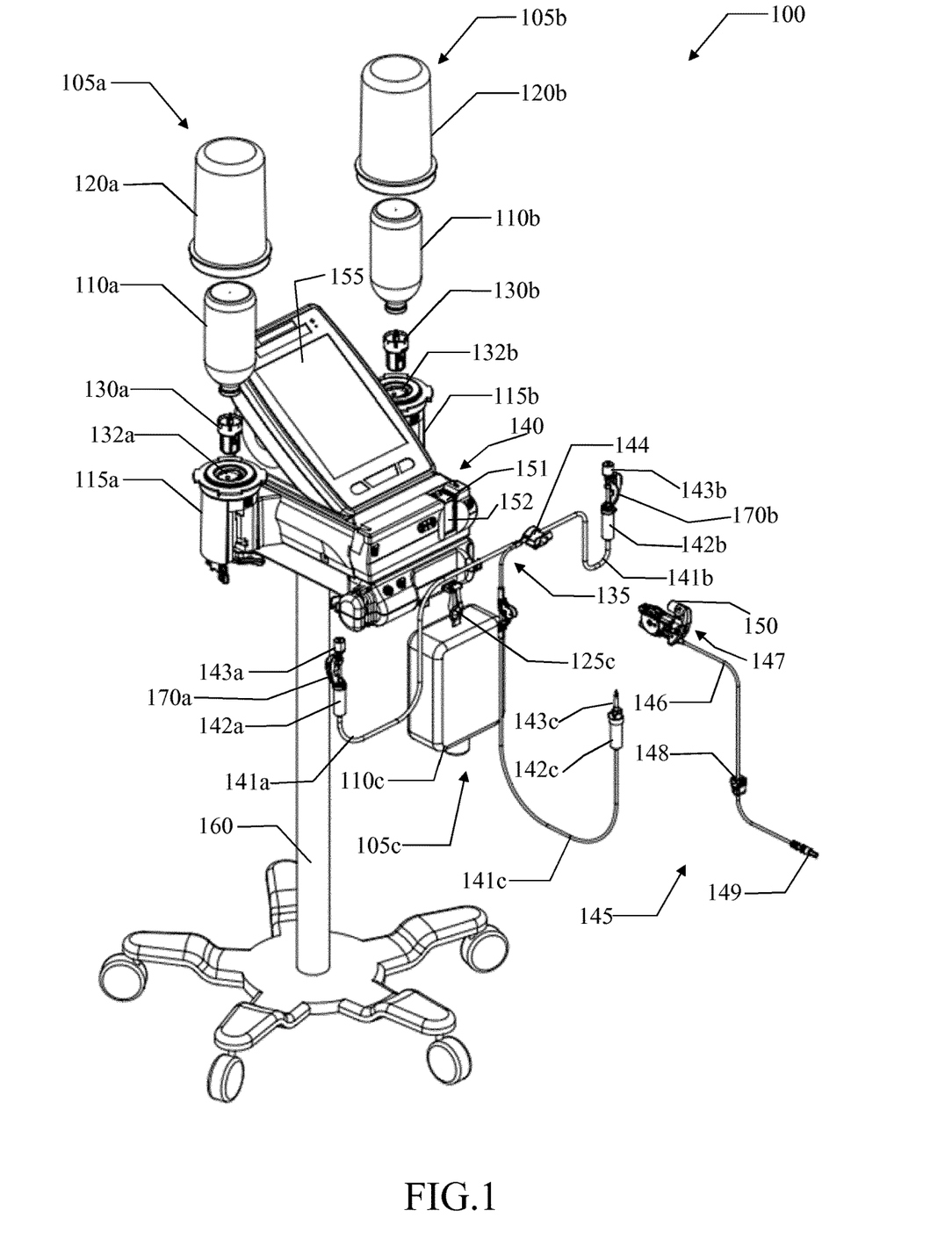
FIG. 1 shows a pictorial representation in a partially exploded view of an injection system wherein the solution according to an embodiment of the present disclosure (not shown in the figure) may be applied.

With reference in particular to FIG. 1, a pictorial representation in partially exploded view is shown of an injection system 100 wherein the solution according to an embodiment of the present disclosure (not shown in the figure) may be applied.

The injection system 100 is used to inject one or more medical fluids into a patient (not shown in the figure); particularly, the injection system 100 is an (automatic) contrast agent and saline solution syringe-less injector that is used by clinicians to perform scan examinations (for example, in radiography applications like CT applications).

The injection system 100 comprises a (left) supply station 105a, a (right) supply station 105b and a (front) supply station 105c for supplying the medical fluids to be injected from corresponding containers. Particularly, the supply station 105a and the supply station 105b supply a medical fluid from a bottle 110a and from a bottle 110b, respectively (for example, made of glass or rigid plastic), whereas the supply station 105c supplies a medical fluid from a pouch 110c (for example, made of soft plastic). The supply stations 105a, 105b may be used to supply one or more contrast agents (to enhance contrast of specific body features within the patient) or a contrast agent and a saline solution (comprising a physiological or isotonic solution), whereas the supply station 105c may be used to supply the saline solution. For example, in CT applications the contrast agent may be a iodine-based contrast agent comprising diatrizoate, ioxaglate, iopamidol, iohexol, ioxilan, iopromide or iodixanol, and the saline solution may be sodium chloride. An example of a commercial contrast agent comprising iopamidol is ISOVUE manufactured by Bracco Diagnostics Inc. (trademarks). Each bottle 110a, 110b may contain a single or multiple dose (for example, 50-500 ml) of different contrast agents (to be supplied in a predetermined sequence) or of the same contrast agent (to be supplied in succession to increase the duration of the scan examination). The pouch 110c generally contains a bulk of saline (for example, 100-1,000 ml) to be supplied before (pre-flush), after (post-flush) or between (interphase) injections of the contrast agent, or alternatively in rapid alternate succession with the contrast agent (to obtain a mixing of the contrast agent and the saline solution within an organ of the patient, for example, the heart). Alternatively, the supply stations 105a and 105b may be used to supply a contrast agent and a saline solution, respectively (without the use of the supply station 105c).

More specifically, each supply station 105a, 105b (respectively) comprises a bottle holder 115a, 115b for the bottle 110a, 110b. A protective cover 120a, 120b may be mounted on the bottle holder 115a, 115b to cover the bottle 110a, 110b when it is held thereon, thereby defining a (closed) chamber for housing the bottle 110a, 110b. The bottle holder 115a, 115b and the protective cover 120a, 120b protect the bottle 110a, 110b from external accidental shocks. Moreover, they are made of a thermally insulating material (for example, polycarbonate) to reduce heat losses, thereby helping to maintain warm (for example, at about the body temperature) the medical fluid contained in the bottle 110a, 110b. The supply station 105c instead simply comprises a hook 125c for hanging the pouch 110c.

A delivery arrangement (also indicated as "transfer set" or "day set" assembly) 135 creates a completely closed fluid pathway for delivering the medical fluids from the containers 110a, 110b, 110c to the patient.

For this purpose, in each supply station 105a, 105b a bottle connector 130a, 130b is arranged in a connection port 132a, 132b of the bottle holder 115a, 115b. The bottle connector 130a, 130b comprises a spike for connecting to the bottle 110a, 110b and a connection element (for example, a septum or a male luer lock fitting) in fluid connection with the spike. The spike and the connection element are located at opposite longitudinal ends of the bottle connector 130a,130b. Typically, the bottle connector 130a, 130b also comprises a filtering unit (not shown in the figure) between its spike and connection element. The bottle connector 130a, 130b is a disposable element for use with a single bottle 110a, 110b (for example, with the spike that breaks off and remains inside the bottle 110a, 110b when the bottle connector 130a, 130b is removed to prevent any accidental re-use thereof).

The delivery arrangement 135 connects all the supply stations 105a, 105b, 105c to a pressurizing unit 140 for transferring the corresponding medical fluids from the containers 110a, 110b, 110c to a patient set assembly 145 which is received inside the pressurizing unit 140. The delivery arrangement 135 comprises a transfer line for each supply station 105a, 105b,105c. The transfer line of each supply station 105a, 105b comprises a flexible tube 141a,141b that is provided (at a distal end thereof with respect to the pressurizing unit 140) with a reservoir (or drip chamber) 142a, 142b and a connection element 143a, 143b for mating with the connection element of the bottle connector 130a, 130b. For example, the connection element 143a,143b is a spike in case the connection element of the bottle connector 130a, 130b is a septum, or the connection element 143a, 143b is a female luer lock fitting in case the connection element of the bottle connector 130a, 130b is a male luer fitting. The reservoir 142a, 142b and the connection element 143a, 143b are arranged inside the bottle holder 115a, 115b. The transfer line of the supply station 105c comprises a flexible tube 141c that is provided (at a distal end thereof with respect to the pressurizing unit 140) with a reservoir (or drip chamber) 142c and a spike 143c for connecting to the pouch 110c. All the flexible tubes 141a, 141b, 141c are coupled (at their proximal ends with respect to the pressurizing unit 140) with a T-connector 144, which comprises a plug for insertion into a corresponding port 151 of the pressurizing unit 140. The delivery arrangement 135 is a disposable element to be changed periodically (for example, every 24 hours).

The pressurizing unit 140 comprises an electric motor (not visible in the figure) for operating a peristaltic pump which is used to pressurize the medical fluids (received from the containers 105a, 105b, 105c via the delivery arrangement 135) for their injection into the patient (for example, up to a pressure of 8 bar or at a flow rate from 0.5 to 9.9 ml/s).

Furthermore, as mentioned above, the injection system 100 comprises a patient set assembly 145 which connects the delivery arrangement 135 to the patient for delivering the (pressurized) medical fluids thereto. The patient set assembly 145 comprises a delivery line made of a flexible delivery tube 146 which is provided (at a distal end thereof with respect to the patient) with a peristaltic pump 147, to be introduced into a dedicated slot 152 provided in the pressurizing unit 140 and also to be put in fluid communication with the T-connector 144 of the delivery arrangement 135. In fact, the peristaltic pump component 147 is provided with a connecting element 150 which fluidically engages with the connecting element 175 of the T-connector 144 in correspondence of port 151 of the pressurizing unit 140. The peristaltic pump 147 houses a rotor having a plurality of squeezing wheels, among which a corresponding portion of the delivery tube 146 is inserted. When the patient set assembly 145 is of single use type (as shown in FIG. 1) for being used by a single patient, the flexible tube 146 is quite long (longer than the tube 146 schematically shown in the figure) and it is provided (at a proximal end thereof with respect to the patient) with a connection element 149 for mating with a respective corresponding connection element (for example, a plug) of a peripheral catheter (not shown in the figure), which is inserted through the skin into a peripheral vein of the patient. The delivery tube 146 can be also provided with a clip 148 that pinches the tube and closes the delivery line during installation or uninstallation of the peripheral catheter.

On the contrary, when the patient set assembly 145 is of multiple use type (not shown in the figure) for use by multiple patients, the delivery tube 146 is quite short and it is provided at the proximal end thereof (with respect to the patient) with a connection element for mating with a corresponding connection element of an additional patient line which typically comprises a quite long flexible tube. The additional patient line terminates (at its proximal end with respect to the patient) with a connection element for mating with a corresponding connection element possessed by the peripheral catheter.

The patient set assembly 145 is a disposable element, which, in case of single use, is for use entirely with a single patient, while, in case of multiple use, it is to be changed periodically (for example, every 12 hours) except for the patient line which is intended for use with a single patient only.

A control unit 155 controls the operation of the injection system 100. For example, the control unit 155 comprises a (main PCB) board with a microprocessor, a RAM that is used as a working memory by the microprocessor and a flash $E^2PROM$ that stores information to be preserved even when a power supply is off (particularly, a control program of the injection system 100). Moreover, the control unit 155 comprises a touch-screen and several buttons, which are used by an operator to interact with it.

The injection system 100 is supported by a stand 160. The stand 160 is provided with wheels to facilitate moving the injection system 100; moreover, the wheels have a foot brake to secure the injection system 100 in position. Alternatively, the injection system is supported by a ceiling or a wall mounting (not shown in the figure), depending on the medical premises needs/requirements where the injection system is installed.

In operation, for each scan examination to be performed, the operator positions the injection system 100 close to the patient and then turns it on. If it has not already been done, the operator installs the delivery arrangement 135 by inserting each reservoir 142a,142b and connection element 143a, 143b into the corresponding bottle holder 115a,115b by acting on a supporting element 170a, 170b provided on the respective flexible tube 141a, 141b. According to the embodiment shown in FIG. 1, the supporting element 170a, 170b is in the form of a bracket which is provided with suitable flaps for a proper and easy handling of the tubes during installation/uninstallation thereof. The supporting element 170a, 170b is typically positioned between the reservoir 142a,142b and connection element 143a, 143b, the reservoir and the connection element being releasably blocked into the corresponding bottle holder therein, for example by means of a snap fitting mechanism. When the pouch 110c (containing the saline solution) is not installed, the control unit 155 displays a message on its screen prompting the operator to do so. If the pouch 110c is to be used, the operator pierces a seal of the pouch 110c with the spike 143c, hangs the pouch 110c from the hook 125c and fills the reservoir 142c completely with the saline solution (by repeatedly squeezing it). At this point, the operator programs the control unit 155 by entering specific information relating to the saline solution of the pouch 110c (for example, its brand name and volume). Otherwise, if the pouch 110c is not used, the operator enters a corresponding command to the control unit 155. In both cases, when the bottle 110a (with the contrast agent) is not installed, the control unit 155 displays a message on its screen prompting the operator to do so. In response thereto, the operator typically takes the bottle 110a from a separate warmer (not shown in the figure), wherein the bottle 110a has been pre-warmed to a target temperature. The target temperature is set to a value high enough to allow injecting the contrast agent efficiently (for example, at the desired flow rate) and comfortably for the patient, but not too high to be harmful for the patient (for example, 32-37.5° C.). Alternatively, no warmer is used and the bottle 110a is installed at ambient temperature. The operator pierces a seal of the bottle 110a with the spike of the bottle connector 130a. Then the operator turns the bottle 110a (with the bottle connector 130a connected thereto) up-side-down, inserts the bottle connector 130a into the connection port 132a (so as to connect its connection element to the connection element 143a), mounts the protective cover 120a on the bottle holder 115a (so as to safely enclose the bottle 110a) and fills the reservoir 142a completely with the contrast agent (by repeatedly squeezing the reservoir 142a). At this point, the operator programs the control unit 155 by entering specific information relating to the contrast agent of the bottle 110a (for example, its brand name and volume). The operator repeats the same operations, if necessary, to install the bottle 110b (with the contrast agent or with the saline solution). The control unit 155 now displays a message on its screen prompting the operator to install the patient set assembly 145. In response thereto, the operator inserts the peristaltic pump 147 into the corresponding slot 152 of the pressurizing unit 140 and connects the peristaltic pump 147 to the T-connector 144. When the patient set assembly 145 is for multiple use, the operator further connects a connection element of the patient line to a corresponding connection element of the delivery line 146. The operator now separately primes each transfer line 141a-143a, 141b-143b and 141c-143c by selecting a corresponding priming function on the control unit 155, so as to eliminate any air bubbles that are possibly present within the transfer lines 141a-143a, 141b-143b and 141c-143c, the delivery line 146 and/or the (possible) patient line. Once this priming phase has been terminated (with no air that is sensed in the injection system 100 any longer), the operator finally connects the connection element 149 of the delivery line 146 (or the connection element of the patient line in case of multi-patient use) to the connection element of the peripheral catheter (already introduced into the patient).

At this point, the operator programs the control unit 155 by entering information relating to the scan examination (for example, a gauge of the needle of the peripheral catheter, an injection profile comprising one or more phases each one defined by the type, volume and flow rate of the medical fluids, possibly selected among pre-defined injection profiles for different types of scan examinations) and then starts the scan examination. At the end of the scan examination, the injection system 100 stops automatically and the operator disconnects the delivery/patient line of the patient set assembly 145 from the peripheral catheter, and then removes and discards it.

Figure 2A:
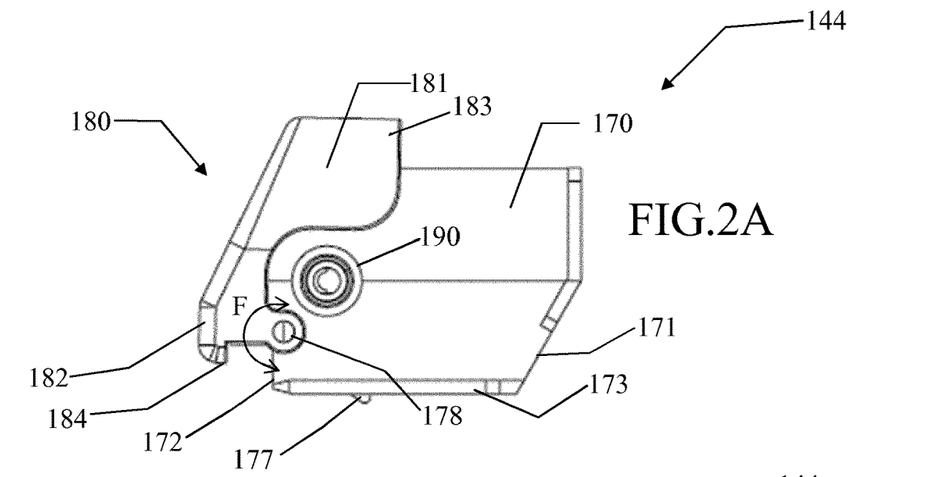
FIGS. 2A-D show, respectively, a lateral view and three perspective views of a connector according to the prior art.
Figure 2B:
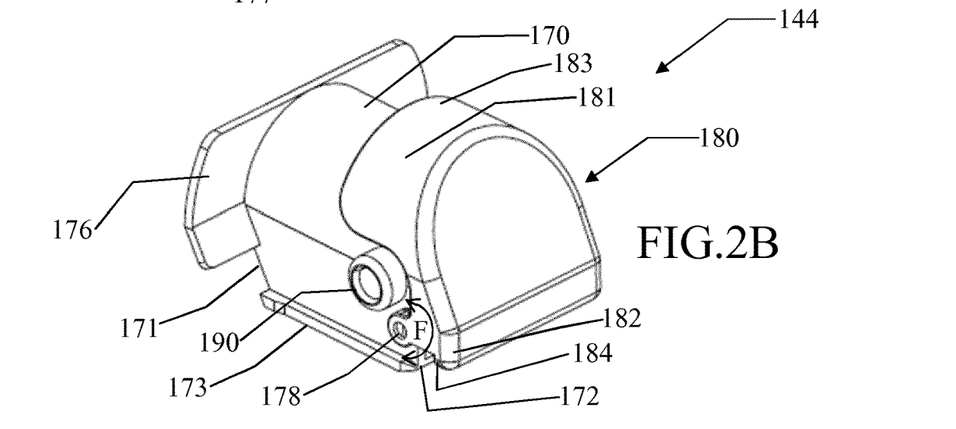
Figure 2C:
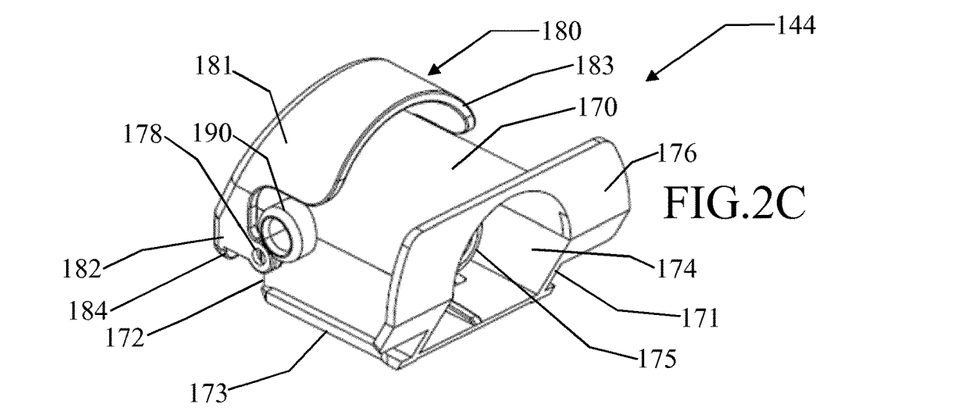

FIGS. 2A-C show pictorial representations in different views of a T-connector 144 known in the art. In detail, FIG. 2A is a lateral view of T-connector 144, while FIG. 2B and FIG. 2C represent, respectively, perspective back and front views of T-connector 144. T-connector 144 comprises a body portion 170 defining a front wall 171, a rear wall 172 and a base component 173. Once the T-connector is properly installed in the dedicated port 151 of the pressurizing unit 140, its front wall 171 faces the operator. The front wall 171 comprises an opening 174 which provides access to a connecting element 175 (partially shown in FIG. 2C) that is positioned inside the body portion 170 and that is suitable for being engaged by the corresponding connecting element 150 of the peristaltic pump 147 of the patient set assembly 145. The front wall 171 further comprises a flange 176 which extends substantially transversally to the base component 173 and which is positioned to surround the opening 174. The flange 176 provides the operator with a suitable support while handling the T-connector during its installation to and uninstallation from the pressurizing unit, thereby avoiding any manipulation and consequent potential contamination of the connecting element 175, especially during installation thereof. The base component 173 is shaped and dimensioned so as to be introduced into the corresponding port 151 of the pressurizing unit 140 and it comprises a protruding tooth 177 (partially shown in FIG. 2A) which is suitable for being sensed by a corresponding position sensor possessed by the pressurizing unit for a proper and correct positioning of the T-connector during operation of the injection system. The rear wall 172 is designed to be at least partially inserted into the dedicated port 151 of the pressurizing unit 140 and it also comprises a latching mechanism 180 for securing the T-connector 144 to said pressurizing unit 140. In detail, the latching mechanism 180 is a distinct component which is separated from the body portion 170, i.e. it is not integral with the body portion 170, and it is associated to the latter by means of a hinge 178 positioned at the rear wall 172 of the T-connector 144. The latching mechanism 180 comprises a pivoting element 181 which can be partially rotated (see arrow F of FIGS. 2A-B) by the operator about the hinge 178 in order to lock the T-connector to and/or to unlock the T-connector from the pressurizing unit of the injection system 100. At a first distal end 182, in proximity of the hinge 178, the pivoting element 181 is provided, along its whole transversal length, with a protruding hooking element 184 which is designed to engage a mating surface possessed by the corresponding port 151 of the pressurizing unit. Therefore, during installation of a new delivery arrangement ("day set" assembly) 135 of the injection system 100, the operator manually holds the T-connector 144 by means of the flange 176 and then he introduces the T-connector inside the corresponding port 151 of the pressurizing unit 140. While pushing the T-connector 144, some ribs (not shown) of the base component 173 interlocks corresponding slots of the pressurizing unit and the protruding tooth 177 is sensed by the corresponding position sensor of the pressurizing unit. Moreover, pushing the T-connector 144 also causes the pivoting element 181 to rotate in the clockwise direction about the hinge 178 and then to counter rotate (in the counter clockwise direction) so that the hooking element 184 engages a mating surface possessed by the pressurizing unit corresponding port 151, thereby safely and properly blocking the T-connector 144 within the pressurizing unit corresponding port 151. Analogously, when a used delivery arrangement ("day set" assembly) 135 has to be discarded to be substituted with a new one, the operator pushes with his finger onto the second distal end 183 of the pivoting element 181, thereby causing rotation thereof (in the clockwise direction) about the hinge 178, and thus releasing the T-connector 144 from the pressurizing unit corresponding port 151. Finally, the operation is completed by pulling the T-connector (typically by acting on the flange 176) and releasing the tooth 177 from the position sensor of the pressurizing unit.

Figure 2D:
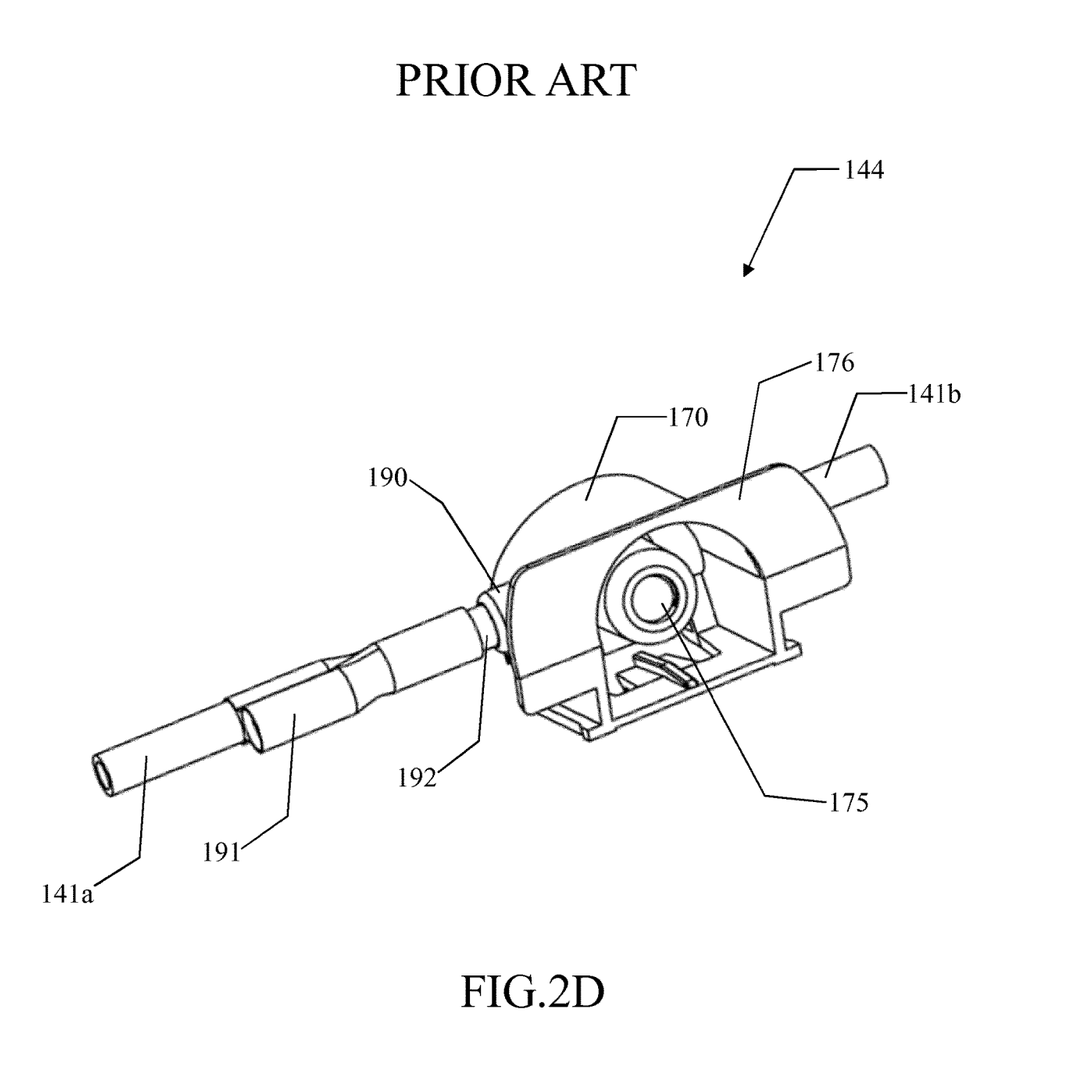

Close to the rear wall 172 and in proximity of the hinge 178, the body portion 170 of the T-connector 144 further comprises a housing 190 for receiving the transfer line of each supply station 105a, 105b, 105c, i.e. the flexible tubes 141a, 141b, 141c. The housing 190 is a tubular conduit passing through the body portion 170 and defining first and second inlet ports on opposite side walls of said body portion 170. The intersection between the connecting element 175 and the housing 190 defines a T-shape intersection which gives the name to the T-connector 144. Moreover, the housing 190 is fluidically connected with the connecting element 175 inside the body portion 170 (such connection is not visible in the figures) so that the fluids contained in the supply stations 105a, 105b, 105c can suitably reach the connecting element 175. In more detail, FIG. 2D shows a Y-tube connector 191 associated (via an additional connecting tube 192) with a first inlet port of the housing 190 so that two distinct tubes (e.g. flexible tubes 141a, 141c according to the embodiment shown in FIG. 1, tube 141c being not shown in FIG. 2D) of the transfer line of the delivery arrangement 135 convey the fluids contained in two separate supply stations (e.g. supply stations 105a, 105c according to the embodiment shown in FIG. 1) into the T-connector 144 and then out of it through the connecting element 175. On the opposite side wall of the body portion 170 (right side in the embodiment shown in FIG. 2D), the housing 190 defines a second inlet port so that a tube (e.g. flexible tube 141b according to the embodiment shown in FIG. 1) of the transfer line of the delivery arrangement 135 conveys the fluid contained in one supply station (e.g. supply station 105b according to the embodiment shown in FIG. 1) into the T-connector 144 and then out of it through the connecting element 175. Typically, the tube of the transfer line of the delivery arrangement 135 enters the second inlet port by means of an additional connecting tube (not shown). The T-connector 144 shown in FIG. 2D does not have the latching mechanism 180 which has been removed for sake of clarity.

Figure 3:
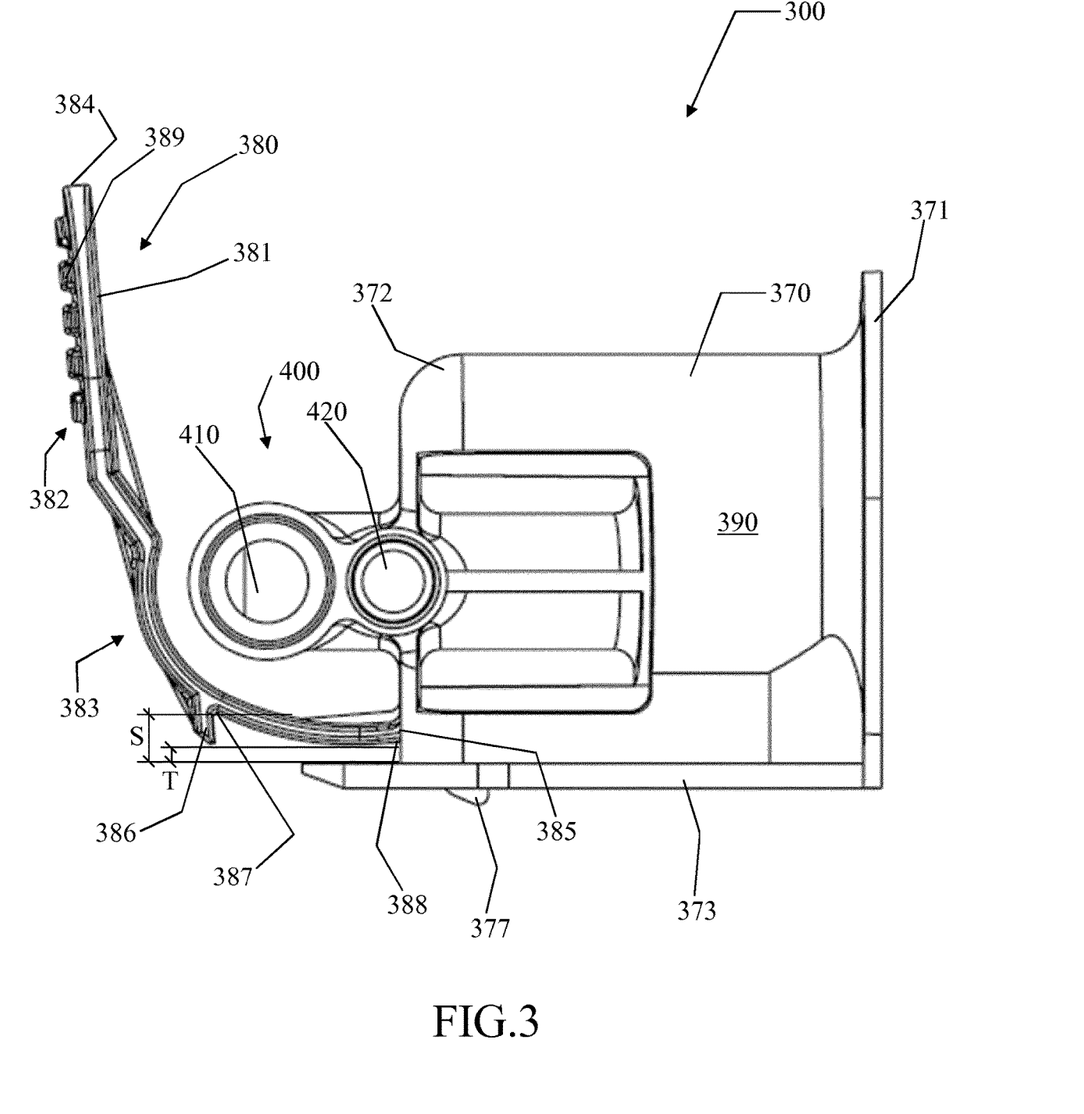
FIG. 3 shows a lateral view of a connector provided to an injection system according to an embodiment of the present disclosure.
Figure 4A:
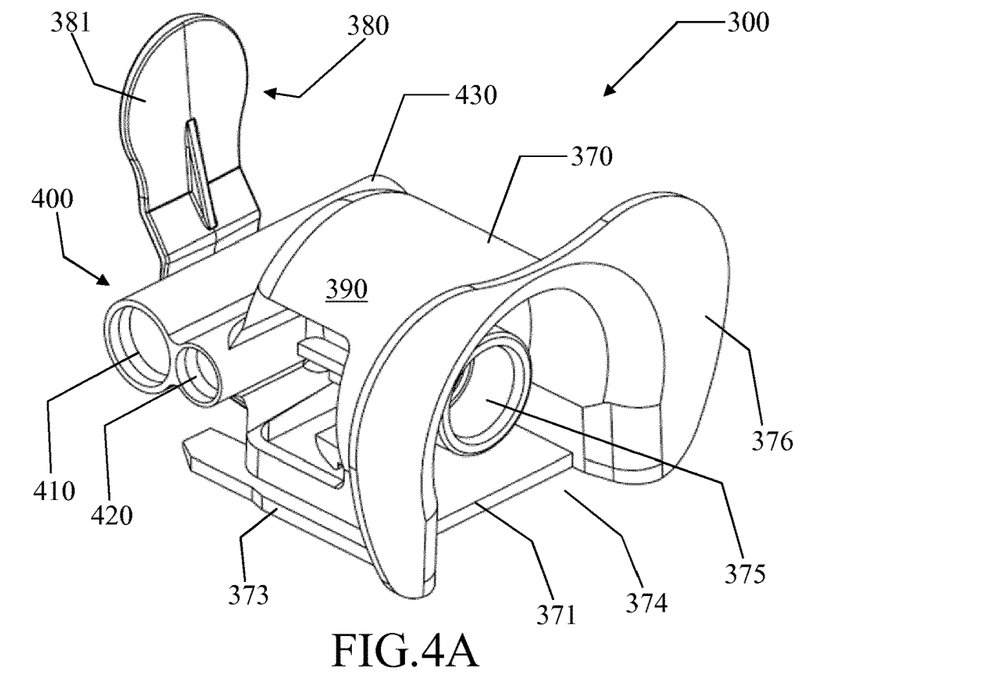
FIGS. 4A-B show perspective views of a connector provided to an injection system according to an embodiment of the present disclosure.
Figure 4B:
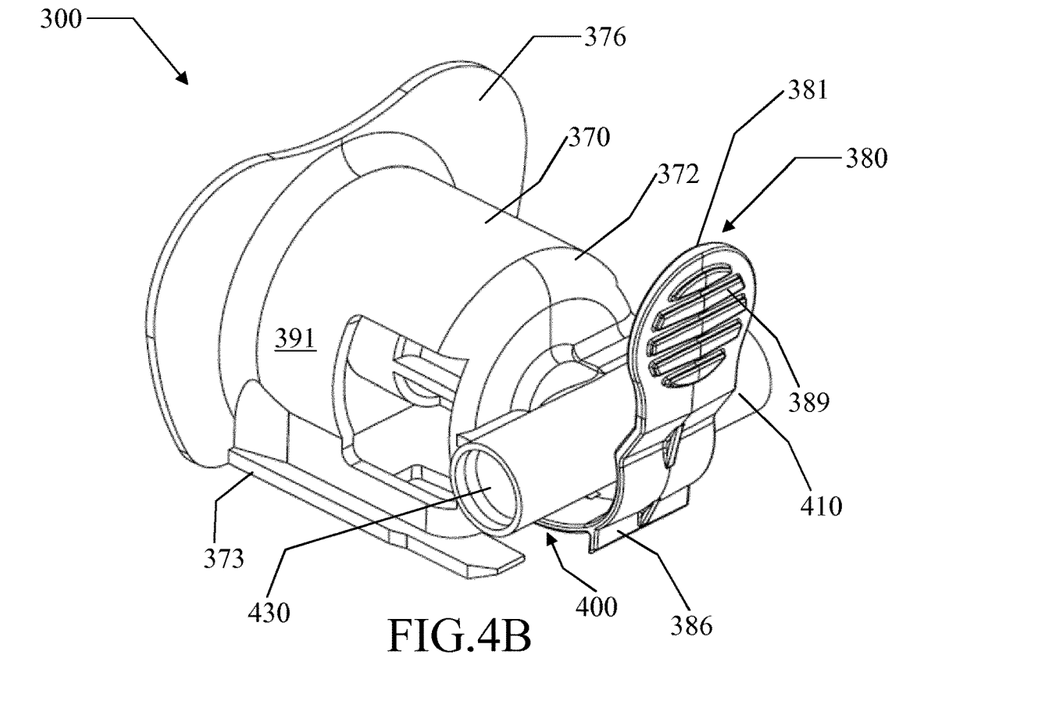

FIGS. 3 and 4A-B show, respectively, a lateral view and two different (front and back) perspective views of a T-connector 300 provided to an injection system according to an embodiment of the present disclosure. In detail, the T-connector 300 comprises a body portion 370 defining a front wall 371, a rear wall 372 and a base component 373. Once the T-connector is properly installed in the dedicated port 151 of the pressurizing unit 140 of the injection system 100, its front wall 371 faces the operator and it comprises an opening 374 which provides access to a connecting element 375 (partially shown in FIG. 4A) that is located within the body portion 370 and that is suitable for being engaged by the corresponding connecting element 150 of the peristaltic pump 147 of the patient set assembly 145. The front wall 371 further comprises a flange 376 which lies in a plane extending substantially transversally to the base component 373. The flange 376 is positioned to surround the opening 374 and it provides the operator with a suitable support for handling the T-connector 300 during its installation to and uninstallation from the injection system pressurizing unit. The base component 373 is shaped and dimensioned so as to be introduced into the corresponding port 151 of the pressurizing unit 140 and it comprises a protruding tooth 377 (partially shown in FIG. 3) which is suitable for being sensed by a position sensor possessed by the pressurizing unit for a proper and correct positioning of the T-connector during operation of the injection system. The rear wall 372 comprises a latching mechanism 380 for securing the T-connector 300 to said pressurizing unit 140.

According to an embodiment of an injection system of the present disclosure, the latching mechanism 380 is integral with the body portion 370 to form a single component that can be advantageously manufactured (e.g. injection molded) in one step, thereby avoiding designing and producing multiple components, as well as assembling thereof. The latching mechanism 380 comprises an elongated flap 381 which is integral with said body portion 370 and which protrudes outwardly from the rear wall 372 of the connector 300. In detail, the elongated flap 381 comprises a first portion 382 and a second portion 383 connected to said first portion 382. The second portion 383 sequentially (consecutively) follows the first portion 383 along the longitudinal development (extension) of the elongated flap 381. The first portion 382, which represents substantially the major part of the elongated flap length, has a straight extension which develops in a direction substantially parallel to the connector front wall 371. The second portion 383 has a curvilinear extension which intersects the connector body portion 370 at its rear wall 372. Moreover, in correspondence of the first portion 382, the elongated flap 381 comprises a free first end 384 which is acted upon by an operator for the connector installation to and/or uninstallation from the pressurizing unit 140, as it will be described in the following disclosure with reference to FIGS. 5A-C. Opposite to the first end 384 and in correspondence of the curvilinear second portion 383, the elongated flap 381 further comprises a second end 385 that integrally associates the latching mechanism 380 to the connector rear wall 372, in proximity of the base component 373.

In order to lock the T-connector 300 to and/or to unlock the T-connector 300 from the pressurizing unit 140 of the injection system 100, closely to the second end 385, the elongated flap 381 comprises a bulge element 386 (better shown in FIG. 3 and FIG. 4B) which is designed to engage a corresponding mating surface possessed by the port 151 of the pressurizing unit 140 into which the T-connector 300 is inserted. The bulge element 386 is provided in the curvilinear second portion 383 of the elongated flap 381 and it protrudes from the external profile of said curvilinear second portion 383 (i.e. it protrudes from the profile of the curvilinear second portion 383 that faces the pressurizing unit 140 of the injection system 100). Moreover, the position of the bulge element 386 along the second curvilinear portion 383 of the elongated flap 381 is designed so that a first point 387 from which said bulge element originates is located at a different level (height) with respect to a second point 388 where the second end 385 of the elongated flap 381 is attached to the rear wall 372 of the connector body portion 370. In more detail, in considering the base component 373 of the connector body portion 370 as a reference system, said first point 387 is positioned at a height S which is greater than the height T of said second point 388. In other words, the position of the axis about which the elongated flap can be flexed, is designed to be lower than the locking position defined by the bulge element 386. This solution (i.e. such geometric configuration) ensures an optimal blocking performance of the bulge element 386 within the corresponding port 151 of the pressurizing unit 140 for a safe and correct functioning of the T-connector 300, and thus of the overall injection system 100.

Furthermore, in proximity of the free first end 384, the first portion 382 of the elongated flap 381 is provided with a gripping surface 389 for advantageously improving the contact of the operator's finger with the elongated flap 381. In more detail, the gripping surface is provided on the external profile of the first portion 382 of the elongated flap 381, i.e. on the profile that faces the pressurizing unit 140 when installed on the injection system 100. It is apparent that the elongated flap 381 should have a suitable length for allowing the operator to easily access it and then to operate on it in the most efficient way. According to an embodiment of the present disclosure (better represented in FIG. 4B), the gripping surface 389 is formed of a plurality of protruding elements which extend in a transversal direction with respect to the longitudinal extension of the elongated flap 381.

According to a further aspect of an injection system of the present disclosure, the body portion 370 of the T-connector 300 further comprises a housing 400 for receiving the transfer line of each supply station 105a, 105b, 105c, i.e. the flexible tubes 141a, 141b, 141c of the injection system 100 shown in FIG. 1. The housing 400 is a tubular element attached to the rear wall 372 of the body portion 370 and it is integral therewith. On opposite side walls of the body portion 370, the housing 400 defines inlet ports for connecting the transfer line of each supply station. In detail, the housing 400 comprises two tubular conduits 410,420 defining two first inlet ports at the first side wall 390 of the body portion 370, and one tubular conduit 430 defining a second inlet port at the second side wall 391 of the body portion 370. According to the embodiment shown in FIG. 3 and FIGS. 4A-B, at the first side wall 390 of the body portion 370 the tubular conduit 410 receives the tube 141a connecting the supply station 105a and the tubular conduit 420 receives the tube 141c connecting the supply station 105c, while at the second side wall 391 of the body portion 370 the tubular conduit 430 receives the tube 141b connecting the supply station 105b.

Moreover, as better shown in FIG. 4A, the housing 400 is fluidically connected with the connecting element 375, that is positioned inside the body portion 370, so that the fluids contained in the supply stations 105a, 105b, 105c can be transferred, through respective transfer lines (i.e. the flexible tubes 141a, 141b,141c), to the T-connector 400 and then to said connecting element 375. The intersection between the connecting element 375 and the housing 400 defines a T-shape intersection which gives the name to the T-connector 400.

According to an embodiment of an injection system of the present disclosure, as better shown in FIG. 3 the second curvilinear portion 383 of the elongated flap 381 has a curvature which at least partially matches the curvature of the housing 400. In more detail, the second curvilinear portion 383 is spaced apart from the housing 400 so that, when operated by the user, there is enough room for the elongated flap 381 to flex and then to release the bulge element 386, as better explained in the following description with reference to FIGS. 5A-C. As said above, the curvature of the inner profile of the second curvilinear portion 383 (i.e. the profile which faces the housing 400) substantially matches the curvature of the most radially external tubular conduits of the housing 400 (i.e. the tubular conduits 410, 430 according to the embodiment shown in the figures).

Figure 5A:
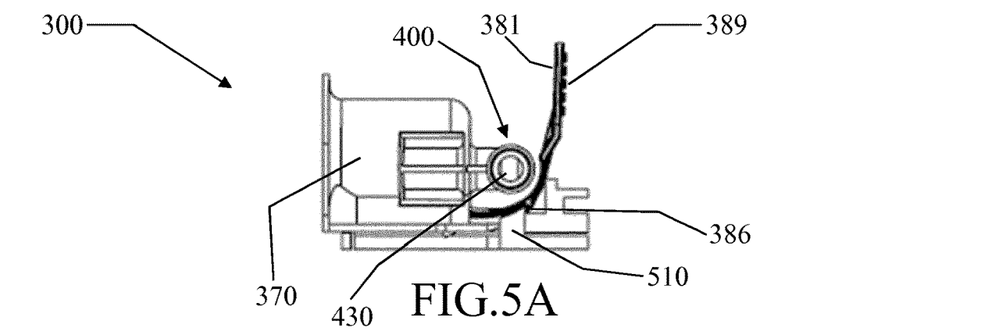
FIGS. 5A-C show lateral views of how the connector is operated to be disengaged from the pressurizing unit of the injector system.
Figure 5B:
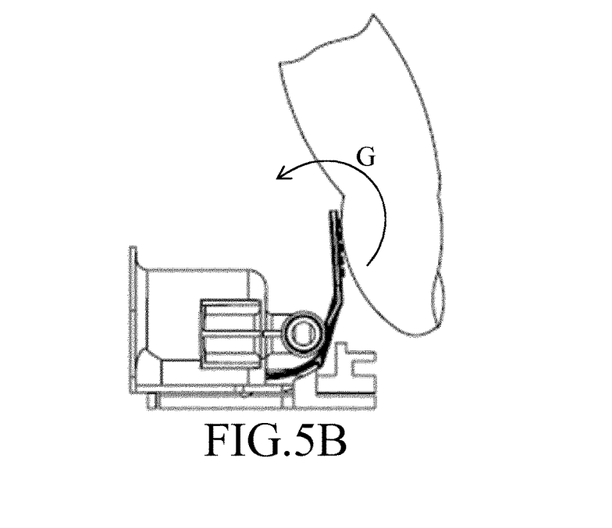
Figure 5C:
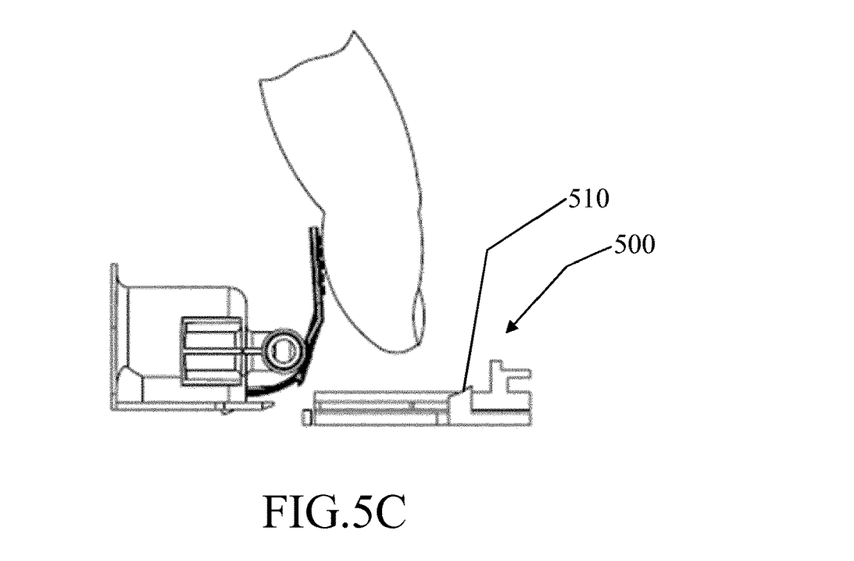

With reference to FIGS. 5A-C, the following description explains how the connector 300 can be easily operated to be released from the pressurizing unit of the injector system. For sake of clarity the pressurizing unit is partially represented in the figures and it only includes a partial view of the portion 500 which is requested to support and to engage the connector 300. As better shown in FIG. 5C, the pressurizing unit portion 500 comprises an engagement surface 510 (a protruding tooth in the embodiment shown in the figures) which is envisaged to interlock with the bulge element 386 of the elongated flap 381.

Therefore, when a delivery arrangement ("day set" assembly) 135 has to be discarded and substituted with a new one, the operator positions his finger on the gripping surface 389 at the free first end 384 of the elongated flap 381 and pushes on it in order to flex the elongated flap 381 towards the connector body portion 370 (i.e. in the direction indicated by arrow G in FIG. 5B). The elongated flap 381 is flexed till its second curvilinear portion 383 comes into contact with the housing 400 and the bulge element 386 is released from the engagement surface 510 of the pressurizing unit portion 500, thereby fully detaching the delivery arrangement ("day set" assembly) 135 from the injector.

Analogously (not shown in the figures), during installation of a new delivery arrangement ("day set" assembly) 135 of the injection system 100, the operator manually holds the T-connector 300 by means of the flange 376 and then he introduces the T-connector 300 inside the corresponding port 151 of the pressurizing unit 140. While pushing the T-connector 300, the protruding tooth 377 of the base component 373 is sensed by a position sensor of the pressurizing unit and the bulge element 386 engages the engagement surface 510 of the pressurizing unit portion 500, thereby fully connecting and blocking the T-connector 300 at the injector.

Figure 6:
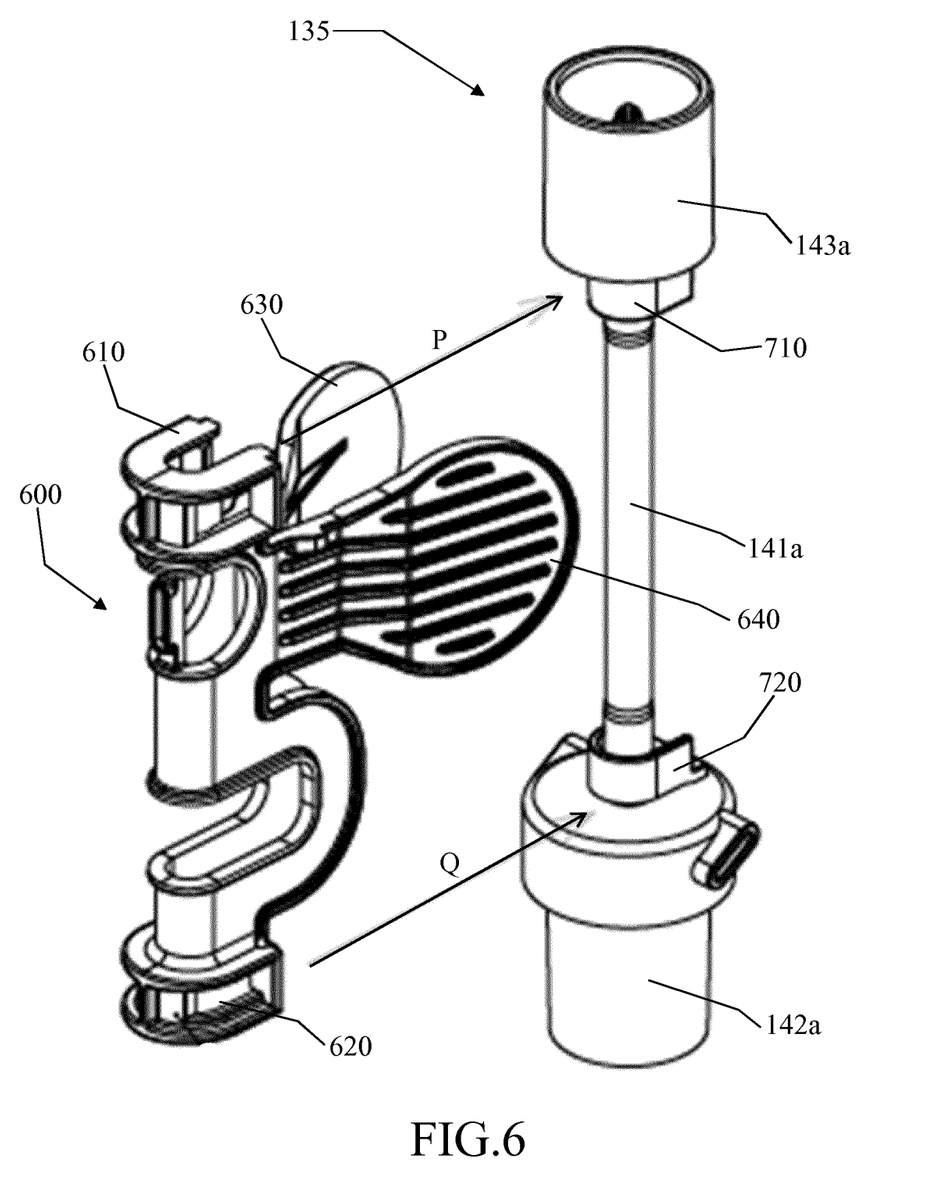
FIG. 6 shows a detail of the delivery arrangement according to an embodiment of the present disclosure.

According to a further aspect of the present disclosure, the transfer line of the delivery arrangement 135 (i.e. the flexible tubes 141a, 141b connecting the respective supply stations 105a, 105b where a bottle container is used) is provided with supporting elements (brackets) 600 (one supporting element for each flexible tube) which allow a correct handling and positioning of the delivery arrangement 135 on the injector. In detail, each supporting element 600 is made of a single plastic component having (in cross-section) a substantially U-shape configuration which allows a tube of the transfer line to enter into the open part of the U-shape configuration and to be fixed at a corresponding supporting element 600. As better shown in FIG. 6, the axial ends of the supporting element 600 comprise clip fittings 610,620 which engage corresponding mating elements 710,720 on the flexible tube (i.e. tube 141a in FIG. 6), thereby properly and safely connecting the supporting element 600 to the respective tube of the transfer line (see arrows P and Q). According to the present disclosure, the supporting element 600 comprises a pair of flaps 630,640 which are used by the operator, during the operations of installation and uninstallation of the delivery arrangement 135, for handling the transfer line and properly inserting it into the bottle holders.

Modifications

In order to satisfy local and specific requirements, a person skilled in the art may apply many logical and/or physical modifications and alterations to the present disclosure. More specifically, although this disclosure has been described with a certain degree of particularity with reference to one or more embodiments thereof, it should be understood that various omissions, substitutions and changes in the form and details as well as other embodiments are possible. Particularly, different embodiments of the present disclosure may even be practiced without the specific details (such as the numerical values) set forth in the preceding description to provide a more thorough understanding thereof. Conversely, well-known features may have been omitted or simplified in order not to obscure the description with unnecessary particulars. Moreover, it is expressly intended that specific elements and/or method steps described in connection with any embodiment of the present disclosure may be incorporated in any other embodiment as a matter of general design choice. In any case, each numerical value should be read as modified by the term about (unless already done) and each range of numerical values should be intended as expressly specifying any possible number along the continuum within the range (comprising its end points). Moreover, ordinal or other qualifiers are merely used as labels to distinguish elements with the same name but do not by themselves connote any priority, precedence or order. The terms include, comprise, have, contain and involve (and any forms thereof) should be intended with an open, non-exhaustive meaning (i.e., not limited to the recited items), the terms based on, dependent on, according to, function of (and any forms thereof) should be intended as a non-exclusive relationship (i.e., with possible further variables involved), the term a/an should be intended as one or more items (unless expressly indicated otherwise), and the term means for (or any means-plus-function formulation) should be intended as any structure adapted or configured for carrying out the relevant function.

In an embodiment, the injection system is for injecting one or more fluids into a patient. However, the fluids may be in any number and of any type (for example, whatever medical fluid to be used in a generic medical application for diagnostic or therapeutic purposes, such as a drug or a body fluid, or more generally to be used in any other treatment, such as for cosmetic purposes); moreover, the fluid may be injected in any way (for example, intra-arterially) into any (human or animal) patient.

In an embodiment, the injection system comprises one or more supply stations each one for supplying one of the fluids to be injected from a container. However, the injection system may comprise any number of supply stations (down to a single one) for supplying the same or different fluids (in any combination); moreover, the container may be of any type, either the same or different in the supply stations (for example, bottles, bags, pouches, syringes and any combination thereof).

In an embodiment, at least one of the supply stations comprises housing means defining a chamber for housing the container. However, the above-described solution may be applied to any number of supply stations (from a single one to all of them); moreover, the chamber may be of any type, shape, size and arranged at any position (for example, enclosing the container completely or only partially, with a hook for hanging it) and it may be defined by any structure (for example, an enclosure with an access door).

In an embodiment, the chamber has a connection port for connecting the container to a delivery arrangement for delivering the fluid to the patient. However, the connection port may be of any type, shape, size and arranged at any position (for example, a valve integral with the bottle holder); moreover, the delivery arrangement may be of any type (for example, with individual transfer lines for each supply station, with a delivery line ending with a needle for direct insertion into the patient).

In an embodiment, the injection system is for injecting the fluids into the patient during a scan examination thereof; the fluids are one or more medical fluids comprising a contrast agent and/or a saline solution. However, the injection system may be used for any scan examination (for example, in MR, nuclear or ultrasound imaging applications); moreover, the injection system may be used with any contrast agent (for example, a barium-based contrast agent such as barium sulfate, gadolinium, a radioisotope, a suspension of gas-filled microbubbles), any saline solution (for example, with the addition of dextrose), any combination thereof or more generally with any medical fluid(s).

Generally, similar considerations apply if the same solution is implemented with an equivalent method by using similar steps with the same functions of more steps or portions thereof, removing some steps being non-essential, or adding further optional steps); moreover, the steps may be performed in a different order, concurrently or in an interleaved way (at least in part).

The invention claimed is:

1. An injection system (100) comprising:
at least one supply station (105a; 105b; 105c) for supplying a fluid to be injected into a patient's vasculature;
a pressurizing unit (140) comprising a motor for pressurizing the fluid received from said at least one supply station (105a; 105b; 105c);
a delivery arrangement (135) in fluid communication with said at least one supply station (105a; 105b; 105c), the delivery arrangement (135) comprising a connector (300) having a connecting element (375) and a latching mechanism (380);
a patient set assembly (145) in fluid communication with said delivery arrangement (135), said patient set assembly (145) comprising a peristaltic pump component (147) and at least one delivery tube (146) for delivering the pressurized fluid to the patient, said peristaltic pump component (147) having a connecting element (150) for fluidically engaging the connecting element (375) of the connector (300) of the delivery arrangement (135) at a port (151) of the pressurizing unit (140), characterized in that said latching mechanism (380) comprises an elongated flap (381) integral with a connector body portion (370) of said connector (300), and said latching mechanism (380) engages a corresponding port (151) of the pressurizing unit (140).

2. The injection system (100) according to claim 1, characterized in that the elongated flap (381) comprises a first straight portion (382) and a second curvilinear portion (383).

3. The injection system (100) according to claim 2, characterized in that the elongated flap (381) comprises a bulge element (386) protruding from an external profile of said second curvilinear portion (383).

4. The injection system (100) according to claim 1, characterized in that the elongated flap (381) comprises a free first end (384) for being acted upon by an operator.

5. The injection system (100) according to claim 4, characterized in that the elongated flap (381) comprises a second end (385), opposite to the first end (384), said second end (385) being integral with the connector body portion (370) of said connector (300).

6. The injection system (100) according to claim 5, characterized in that the connector body portion (370) defines a front wall (371) and a rear wall (372), the second end (385) of the elongated flap (381) being integral with said rear wall (372).

7. The injection system (100) according to claim 6, characterized in that the connector (300) comprises a housing (400) for receiving at least one tube of the delivery arrangement (135), said housing (400) being integral with the connector body portion (370).

8. The injection system (100) according to claim 7, characterized in that the housing (400) is integral with the rear wall (372) of the connector body portion (370).

9. The injection system (100) according to claim 7, characterized in that the elongated flap (381) comprises a first straight portion (382) and a second curvilinear portion (383) and characterized in that a curvature of the second curvilinear portion (383) at least partially matches a curvature of the housing (400).

10. The injection system (100) according to claim 7, characterized in that the elongated flap (381) comprises a first straight portion (382) and a second curvilinear portion (383) and characterized in that the second curvilinear portion (383) is spaced apart from the housing (400).

11. The injection system (100) according to claim 5, characterized in that the connector body portion (370) defines a front wall (371) and a rear wall (372) and characterized in that the elongated flap (381) comprises a first straight portion (382) and a second curvilinear portion (383) and characterized in that the elongated flap (381) comprises a bulge element (386) protruding from an external profile of said second curvilinear portion (383) and characterized in that a first point (387) from which said bulge element (386) is originated is positioned at a different level with respect to a second point (388) where the second end (385) of the elongated flap (381) is attached to the rear wall (372) of the connector body portion (370).

12. The injection system (100) according to claim 11, characterized in that, with reference to a base component (373) of the connector body portion (370), said first point (387) is positioned at a height greater than a height of said second point (388).

13. The injection system (100) according to claim 4, characterized in that, in proximity of said free first end (384), an outer profile of said elongated flap (381) is provided with a gripping surface (389).

14. The injection system (100) according to claim 1, characterized in that the delivery arrangement (135) comprises at least one supporting element (600) which is made of a single component and which has a substantially U-shape configuration in cross-section.

15. The injection system (100) according to claim 1, characterized in that the connector (300) comprises a housing (400) for receiving at least one tube of the delivery arrangement (135), said housing (400) being integral with the connector body portion (370).

* * * * *